United States Patent [19]

Tsai et al.

[11] 4,319,033
[45] Mar. 9, 1982

[54] METHOD OF MAKING CERTAIN 2,3-DIHYDRO-1,4-DITHIINS

[75] Inventors: Allan K. S. Tsai, Waterloo; Duncan D. Lennox, Elmira; Arthur D. Brewer, Puslinch, all of Canada

[73] Assignee: Uniroyal Ltd., Ontario, Canada

[21] Appl. No.: 247,670

[22] Filed: Mar. 26, 1981

[30] Foreign Application Priority Data

Dec. 2, 1980 [CA] Canada .................................. 365995

[51] Int. Cl.$^3$ ........................................... C07D 335/02
[52] U.S. Cl. ....................................... 549/15; 549/20; 549/21; 549/22
[58] Field of Search ........................ 549/15, 20, 21, 22

[56]  References Cited

U.S. PATENT DOCUMENTS 3,920,438  11/1975  Brewer et al. ..................... 549/21 X
4,004,018  1/1977  Brewer et al. ..................... 549/20 X Primary Examiner—Richard Raymond
Attorney, Agent, or Firm—James J. Long

[57] ABSTRACT

A method of making certain 2,3-dihydro-1,4-dithiins of the following formula by the action of alpha-hydroxyketones (acyloins) of 1,2-dithiols:

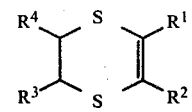

wherein $R^1$ and $R^2$ are hydrogen or alkyl having 1 to 6 carbon atoms or are joined together to form a ring with 3 or 4 methylene groups, and $R^3$ and $R^4$ are hydrogen or the same or different alkyl groups having 1 to 10 carbon atoms, which alkyl groups may be substituted with lower alkoxy groups.

10 Claims, No Drawings

METHOD OF MAKING CERTAIN 2,3-DIHYDRO-1,4-DITHIINS

This invention relates to a novel method of making 2,3-dihydro-1,4-dithiins of formula

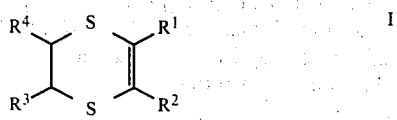

wherein:
$R^1$ and $R^2$ are selected from hydrogen or the same or different alkyl groups having from 1 to 6 carbon atoms, or are joined together to form a ring with 3 or 4 methylene groups;
$R^3$ and $R^4$ are selected from hydrogen or the same or different alkyl groups having from 1 to 10 carbon atoms, which alkyl groups may be substituted themselves with lower alkoxy groups. The method comprises reacting an alpha-hydroxyketone of formula $$R^1COCHOHR^2$$

wherein $R^1$ and $R^2$ are as above defined with a 1,2-dithiol of formula $$HSCHR^3CHR^4SH$$

wherein $R^3$ and $R^4$ are as above defined. The reaction is accompanied by evolution of water.

Previously disclosed methods of synthesis include the reaction of alpha-haloketones with 1,2-dithiols (U.S. Pat. No. 3,920,438, Nov. 18, 1975 Brewer et al):

$$R^1COCHXR^2 + HSCHR^3CHR^4SH \longrightarrow \text{Method i}$$

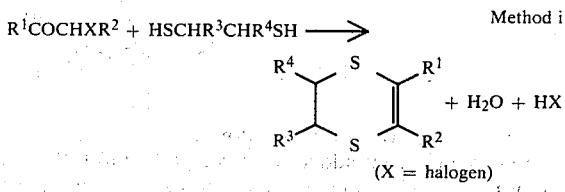

(X = halogen)

and the reaction of a ketone with a dithiol to give a 1,3-dithiolane which is subsequently converted to a 1,4-dithiin by the action of halogen (U.S. Pat. No. 3,920,438 cited above):

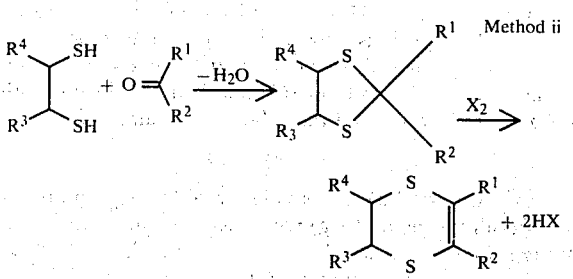

These methods disclosed in the prior art have several disadvantages. They involve the use of poisonous, corrosive and expensive halogenating reagents, such as chlorine, bromine or sulfuryl chloride, which necessitate the use of expensive glass-lined apparatus and elaborate protective measures for personnel. They also generate two molecular equivalents of hydrogen halide which must be disposed of in an ecologically acceptable manner, at considerable expense. Furthermore, the methods disclosed in the prior art are limited in their synthetic applicability; because unsymmetrical ketones cannot be specifically halogenated in one position (J. Chem. Soc., 1984, 272, 276, 278), giving mixtures which may not be separable even by arduous fractional distillation, dithiins of Formula I, where $R^1$ and $R^2$ are the same alkyl group (other than methyl) are not accessible. Halogenation of symmetrical ketones, which does give one unique haloketone product, produces only unsymmetrically substituted dithiins; $R^1$ cannot be the same as $R^2$. A similar disadvantage pertains to Method ii above, where dithiolanes with $R^1$ and $R^2$ different inevitably give rise to mixtures of products which cannot be separated.

By contrast, the present method does not involve any halogenating agents and produces as by-product only two molecular equivalents of water, according to the equation $$HSCHR^3CHR^4SH + R^1COCHOHR^2 \longrightarrow$$

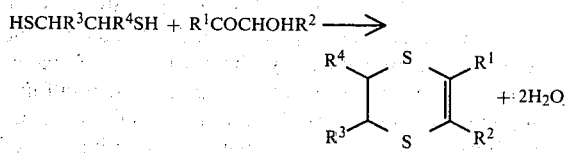

Consequently equipment costs and pollution abatement charges are significantly reduced. Furthermore, since symmetrically-substituted hydroxyketones of type $$R^1COCHOHR^2$$

wherein $R^1$ and $R^2$ are the same lower alkyl groups are readily available from a variety of synthetic procedures, symmetrically-substituted dithiins are readily accessible. The present process is, however, also applicable with equal ease to the synthesis of unsymmetrically substituted dithiins.

Among the 2,3-dihydro-1,4-dithiins that may be made by the method of the invention there may be mentioned 2,3-dihydro-5-methyl-1,4-dithiin, 2,3-dihydro-2,5-dimethyl-1,4-dithiin, 2,3-dihydro-2,6-dimethyl-1,4-dithiin, 2-ethyl-2,3-dihydro-5-methyl-1,4-dithiin, 2-ethyl-2,3-dihydro-6-methyl-1,4-dithiin, 2,3-dihydro-5,6-dimethyl-1,4-dithiin, 2,3-dihydro-2,5,6-trimethyl-1,4-dithiin, 2,3-dihydro-2,3,5,6-tetramethyl-1,4-dithiin, 2-ethyl-2,3-dihydro-5,6-dimethyl-1,4-dithiin, 2,3-diethyl-5,6-dihydro-1,4-dithiin, 5,6-dihydro-1,4-dithiin, 5,6-diethyl-2,3-dihydro-2-methyl-1,4-dithiin, 2,5,6-triethyl-2,3-dihydro-1,4-dithiin, 2,3-dihydro-5,6-dipropyl-1,4-dithiin, 2,3-dihydro-2-methyl-5,6-dipropyl-1,4-dithiin, 2-ethyl-2,3-dihydro-5,6-dipropyl-1,4-dithiin, 2,3-dibutyl-5,6-dihydro-1,4-dithiin, 5,6-dibutyl-2,3-dihydro-2-methyl-1,4-dithiin, 5,6-dibutyl-2-etihyl-2,3-dihydro-1,4-dithiin, 2,3-dihydro-5,6-dipentyl-1,4-dithiin, 2,3-dihydro-2-methyl-5,6-dipentyl-1,4-dithiin, 2-ethyl-2,3-dihydro-5,6-dipentyl-1,4-dithiin, 2,3-dihexyl-5,6-dihydro-1,4-dithiin, 5,6-dihexyl-2,3-dihydro-2-methyl-1,4-dithiin, 2-ethyl-5,6-dihexyl-2,3-dihydro-1,4-dithiin, 2,3-dihydro-5,6-di(2-methylpropyl)-1,4-dithiin, 2,3-dihydro-2-methyl-5,6-di(2-methylpropyl)-1,4-dithiin, 2-ethyl-2,3-dihydro-5,6-di(2-methylpropyl)-1,4-dithiin, 2,3-dihydro-2-propoxymethyl-5,6-dimethyl-1,4-dithiin, 2,3-dihydro-5,6-dimethyl-2-((1-methylethoxy)-methyl)-1,4-dithiin, 2-decyl-5,6-diethyl-2,3-dihydro-1,4-dithiin, 5,6,7,8-tetrahydro-1,4-benzodithian, 5,6,7,8-tetrahydro-2-methyl-1,4-benzodithian, and 2-ethyl-5,6,7,8-tetrahydro-1,4-benzodithian.

The process of the invention is carried out by bringing together an alpha-hydroxyketone of the formula

R¹COCHOHR² and a 1,2-dithiol of the formula

HSCHR³CHR⁴SH where $R^1$ and $R^2$ are hydrogen or the same or different alkyl groups having from 1 to 6 carbon atoms (including both straight chain and branched alkyl groups), or are joined together to form a ring with 3 or 4 methylene groups, and $R^3$ and $R^4$ are selected from hydrogen or the same or different alkyl groups having from 1 to 10 carbon atoms, which alkyl groups may be substituted with lower alkoxy groups (e.g., 1 or 2 alkoxy groups having 1 to 3 carbon atoms). Usually the process is carried out in the presence of an organic solvent, such as benzene, toluene or xylene. As indicated above, the reaction is accompanied by the formation of water. Presence of an acidic catalyst (e.g, p-toluenesulfonic acid, methanesulfonic acid, naphthalenesulfonic acid, polyphosphoric acid) encourages the splitting off of water. Although the process may be conducted at room temperature, or event below room temperature (e.g. 0° C.), the reaction mixture is usually heated to an elevated temperature (e.g., heated to a temperature of up to 180° C.). Frequently the reaction mixture is heated at refluxing temperature. It is advantageous to remove the evolved water, especially toward the end of the reaction, to bring the reaction to substantial completion. Conveniently the water is removed azeotropically, relying on the solvent medium as the azeotrope former. Upon substantial completion of the reaction (usually within, for example, from ½ to 10 hours) the 2,3-dihydro-1,4-dithiin of the above formula formed by the reaction can be separated from the reaction mixture by conventional methods. The product is particularly useful for conversion (by oxidation in the conventional manner) to the corresponding 2,3-dihydro-1,4-dithiin-1,1,4,4-tetroxides, which are valuable plant growth regulants (U.S. Pat. No. 3,920,438, cited above). Surprisingly, the product made by the method of this invention can be oxidised without distillation, whereas the product made by the prior process, if subjected to identical conditions, gives a much poorer yield of product which is, in addition, unacceptably impure.

The following examples will serve to illustrate the practice of the invention in more detail.

EXAMPLE 1

Acetoin (44 g), 1,2-ethanedithiol (47.1 g) and methanesulfonic acid (70%, 4.9 g) were dissolved in toluene (170 g) and the solution kept at 60°–75° for 1.1 hours. Water (18.3 g, calc. 18.0 g) was evolved. On removal of the solvent there was obtained a 91.1% yield of 2,3-dihydro-5,6-dimethyl-1,4-dithiin. NMR(CDCl₃) 1.86 δ (singlet), 3.12 δ (singlet). This result is particularly unexpected in view of the fact that if it is attempted to carry out the following synthesis in a similar manner, the process does not work:

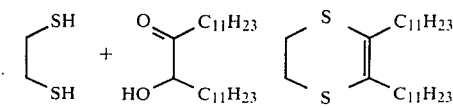

Therefore the present process is not predictable or obvious from Marshall and Stevenson, J. Chem. Soc., 1959, 2360, who reported that the yield obtained was poor in the following synthesis:

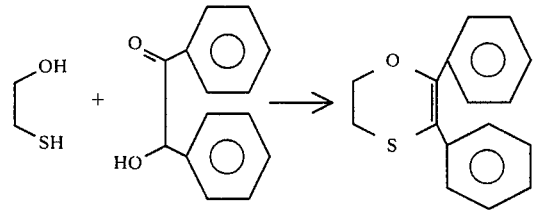

(See also U.S. Pat. No. 3,947,264, Mar. 30, 1976, Graham et al; also copending application Ser. No. 157,725, filed June 9, 1980 Puttock et al.) The difficulty of predicting how a particular hydroxyketone will react with a dithiol, is emphasized by the fact that if the following reaction is attempted by subjecting the reagents to the kind of conditions which give good yields in the above Example 1, there is obtained only a negligible yield:

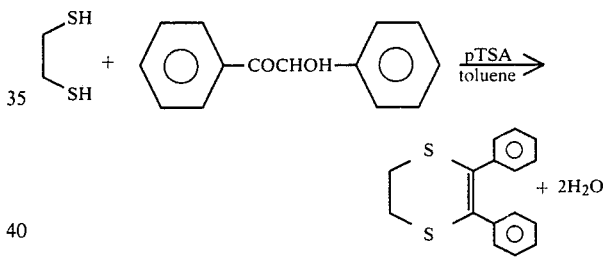

Such an experiment is as follows:

Benzoin (30 g) is added to toluene (200 ml) followed by p-toluenesulphonic acid hydrate (0.5 g) and ethane dithiol (13.3 g). The solution is refluxed under a Dean-Stark trap for 80 minutes. At the end of this time only a trace (ca. 0.2 ml) of water has appeared, most of which is attributable to water of hydration in the catalyst and water in the ethane dithiol. On cooling, a solid begins to crystallise; mp 105°–126°, mixed mp with benzoin 105°–128° [i.e. it is substantially unchanged benzoin]. The filtrate has the characteristic vile odour of unchanged ethane dithiol. (Compare these results with Example 1 above and the following Example 2.)

EXAMPLE 2

Acetoin (43.5 g), 1,2-ethanedithiol (46.6 g) and p-toluenesulfonic acid (3.8 g) were dissolved in toluene, and the solution kept at 70°–78° for 1 hour. Water (18.0 g, calc. 18.0 g) was evolved. On removal of the solvent there was obtained a 94.7% yield of 2,3-dihydro-5,6-dimethyl-1,4-dithiin, NMR as in Example 1.

EXAMPLE 3

Butyroin (10 g) 1,2-ethanedithiol (6.7 g) and p-toluenesulfonic acid (0.5 g) were dissolved in toluene (50 g) and the solution refluxed under a Dean-Stark trap.

Water (1.1 g, calc. 1.28 g) slowly collected. The solution was cooled, washed with dilute aqueous sodium bicarbonate solution, dried, the solvent removed and the oily residue distilled at reduced pressure. The fraction boiling between 80° and 104° at 0.03 mm proved to be 2,3-dihydro-5, 6-dipropyl-1,4-dithiin, yield 5.5 g (38%). NMR(CDCl$_3$) 0.93 δ (triplet) 1.23–1.85 δ (multiplet), 2.11–2.38 δ (complex quartet), 3.14 δ (singlet).

EXAMPLE 4

Butyroin (12.2 g), butane-1,2-dithiol (14.4 g) and p-toluenesulfonic acid (0.5 g) were dissolved in toluene (50 g) and the solution refluxed under a Dean-Stark trap. It was worked up as in Example 3 to give 2-ethyl-2,3-dihydro-5,6-dipropyl-1,4-dithiin as a clear greenish liquid, boiling range 92°–105°/0.025 mm, yield 8.5 g (44%). NMR(CDCl$_3$), 0.78–1.14 δ (overlapping triplets), 1.21–1.80 δ (multiplet) 2.07–2.37 δ (complex quartet), 2.6–3.4 δ (multiplet).

EXAMPLE 5

The method of Example 4 was followed, using butyroin (12 g), propane-1,2-dithiol (9 g) and p-toluenesulfonic acid (0.5 g). 2,3-Dihydro-2-methyl-5,6-dipropyl-1,4-dithiin was obtained as a greenish liquid, boiling range 76°–85°/0.055 mm, yield 7.5 g (35%). NMR (CDCl$_3$) 0.92 δ (triplet), 1.25–2.4 δ (complex overlapping doublet, multiplet, and quartet) 2.6–3.6 δ (complex multiplet).

EXAMPLE 6

The method of Example 4 was used, using valeroin (17.2 g) ethane-1,2-dithiol (9.4 g) and p-toluenesulphonic acid (0.5 g). 2,3-Dibutyl-5,6-dihydro-1,4-dithiin was obtained as a greenish oil, bp 95°–110°/0.04 mm, yield 66.3%. NMR (CDCl$_3$) 3.12 δ (singlet), 0.7–2.4 δ (complex series of multiplets in 3 groups).

EXAMPLE 7

The method of Example 4 was used, using 7-hydroxytetradecan-8-one (22.8 g), ethane dithiol (9.4 g) and p-toluenesulphonic acid (0.5 g) to give 2,3-dihexyl-5,6-dihydro-1,4-dithiin as a greenish oil, bp 145°–155°/0.09 mm, yield 67.8%. NMR (CDCl$_3$) 3.13 δ (singlet), 0.7–2.4 δ (complex series of multiplets).

EXAMPLE 8

The method of Example 4 was used, using 7-hydroxytetradecan-8-one (22.8 g), propane-1,2-dithiol (10.8 g) and p-toluenesulphonic acid (0.5 g) to give 2,3-dihexyl-5,6-dihydro-5-methyl-1,4-dithiin as a greenish oil, bp 148°–155°/0.2 mm, yield 63%. NMR, 0.7–1.8 δ (multiplets), 2.05–2.35 δ (broad triplet), 2.45–3.6 δ (multiplets), 2.95 δ (doublet).

EXAMPLE 9

The method of Example 4 was used, using 2-hydroxycyclohexanone (10 g), ethane dithiol (8.3 g) and p-toluenesulphonic acid to give 5,6,7,8-tetrahydro-1,4-benzodithian as a brownish oil (not distilled), yield 75.1%. NMR (CDCl$_3$) 3.14 δ, 1.5–2.3 δ (two overlapping complex multiplets).

EXAMPLE 10

The method of Example 4 was used, using acetol (47 g), ethane dithiol (37 g) and p-toluenesulphonic acid (0.5 g), to give 2,3-dihydro-5-methyl-1,4-dithiin as a greenish oil, bp 93°–120°/40 mm, yield 63.4%. NMR (CDCl$_3$) 5.83 δ (quartet), 3.14 δ (narrow multiplet), 1.92 δ (doublet).

EXAMPLE 11

The method of Example 4 was used, using isovaleroin (25 g), ethane dithiol (13.7 g) and p-toluenesulphonic acid (0.5 g), to give 2,3-dihydro-5,6-di(2-methylpropyl)-1,4-dithiin as a greenish oil, bp 96°–112°/0.18 mm, yield 61%. NMR 3.13 δ (singlet), 1.6–2.3 δ (multiplets), 0.95 δ (doublet).

EXAMPLE 12

The method of Example 4 was followed using propioin (4-hydroxy-3-hexanone) (11.6 g) and 3(1-methylethoxy)-propane-1,2-dithiol (16.6 g) to give 5,6-diethyl-2,3-dihydro-2-(1-methylethoxy) methyl)-1,4-dithiin as a greenish oil, b.p. 80°–100°/0.2 mm, yield 23%. NMR (CDCl$_3$) 0.98–1.22 δ (overlapping doublet and triplet), 2.18 δ (triplet), 2.98–3.71 δ (overlapping multiplets).

EXAMPLE 13

The method of Example 4 was followed, using propioin (4-hydroxy-3-hexanone) (11.6 g) and 3-propoxypropane-1,2-dithiol (16.6 g) to give 5,6-diethyl-2,3-dihydro-2-propoxymethyl-1,4-dithiin as a greenish oil, b.p. 110°–111.5°/0.2 mm, yield 42%. N.M.R. (CDCl$_3$) 0.8–1.25 δ triplets), 1.6–1.95 δ (complex overlapping signals), 2.75–3.65 δ (complex overlapping signals).

EXAMPLE 14

The method of Example 4 was followed using propioin (4-hydroxy-3-hexanone) (8.2 g) and dodecane-1,2-dithiol (15.1 g) to give 2-decyl-5,6-diethyl-2,3-dihydro-1,4-dithiin as an undistillable oil, yield 58%. NMR, (CDCl$_3$) 0.8–1.28 δ (overlapping triplets), 1.38 δ (broadened singlet), 2.05–2.41 δ (quartet), 2.7–3.38 δ (multiplet).

What is claimed is:

1. A method of making a 2,3dihydro-1,4-dithiin of the formula

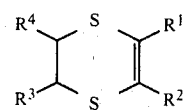

wherein:
   $R^1$ and $R^2$ are selected from hydrogen or the same or different alkyl groups having from 1 to 6 carbon atoms, or are joined together to form a ring with 3 or 4 methylene groups;
   $R^3$ and $R^4$ are selected from hydrogen or the same or different alkyl groups having from 1 to 10 carbon atoms, which alkyl groups may be substituted themselves with lower alkoxy groups, comprising bringing together a 1,2-dithiol of the formula $HSCHR^3CHR^4SH$ and an alpha-hydroxyketone of the formula $R^1CHOHCOR^2$ wherein $R^1$, $R^2$, $R^3$ and $R^4$ are as above defined, whereby water is evolved and a dihydrodithiin of the said formula is produced.

2. A method as in claim 1 wherein the reaction is carried out with an acid catalyst.

3. A method as in claim 2 wherein the catalyst is p-toluenesulfonic acid.

4. A method as in claim 2 wherein the catalyst is methanesulfonic acid.

5. A method as in claim 1 wherein the water of reaction is removed azeotropically.

6. A method as in claim 5 wherein a solvent chosen from benzene, toluene or xylene is present in the reaction mixture.

7. A method as in claim 1 wherein $R^1$ and $R^2$ are methyl groups and $R^3$ and $R^4$ are hydrogen atoms.

8. A method as in claim 1 wherein $R^1$, $R^2$ and $R^3$ are methyl groups, and $R^4$ is a hydrogen atom.

9. A method as in claim 1 wherein $R^1$ and $R^2$ are methyl groups, $R^3$ is an ethyl group and $R^4$ is a hydrogen atom.

10. A method as in claim 1 wherein the dihydrothiins so made are converted to the corresponding oxidised dithiins by treatment with an appropriate oxidising agent.

* * * * *